United States Patent
Trier et al.

(10) Patent No.: US 9,421,386 B2
(45) Date of Patent: Aug. 23, 2016

(54) DIVERSITY ANTENNAS FOR NEUROSTIMULATOR PROGRAMMING DEVICES

(71) Applicant: Nuvectra Corporation, Plano, TX (US)

(72) Inventors: Stephen C. Trier, Mayfield Heights, OH (US); Raymond Lloyd Yoder, Willoughby, OH (US)

(73) Assignee: Nuvectra Corporation, Plano, TX (US)

( * ) Notice: Subject to any disclaimer, the term of this patent is extended or adjusted under 35 U.S.C. 154(b) by 0 days.

(21) Appl. No.: 14/670,539

(22) Filed: Mar. 27, 2015

(65) Prior Publication Data

US 2015/0202450 A1     Jul. 23, 2015

Related U.S. Application Data

(62) Division of application No. 13/442,283, filed on Apr. 9, 2012, now Pat. No. 9,002,466.

(51) Int. Cl.

| | |
|---|---|
| *A61N 1/372* | (2006.01) |
| *H01Q 1/24* | (2006.01) |
| *H01Q 1/27* | (2006.01) |
| *H01Q 21/28* | (2006.01) |
| *H04B 7/06* | (2006.01) |
| *H04B 7/08* | (2006.01) |
| *H04B 7/12* | (2006.01) |
| *A61N 1/36* | (2006.01) |

(52) U.S. Cl.
CPC ........ *A61N 1/37223* (2013.01); *A61N 1/37211* (2013.01); *A61N 1/37229* (2013.01); *A61N 1/37235* (2013.01); *H01Q 1/243* (2013.01); *H01Q 1/273* (2013.01); *H01Q 21/28* (2013.01); *H04B 7/0686* (2013.01); *H04B 7/0868* (2013.01); *H04B 7/12* (2013.01); *A61N 1/36071* (2013.01)

(58) Field of Classification Search
None
See application file for complete search history.

(56) References Cited

U.S. PATENT DOCUMENTS

| | | | | |
|---|---|---|---|---|
| 5,926,139 | A * | 7/1999 | Korisch | H01Q 1/243 343/700 MS |
| 6,167,312 | A | 12/2000 | Goedeke | |
| 6,240,317 | B1 | 5/2001 | Villaseca et al. | |
| 6,893,395 | B1 | 5/2005 | Kraus et al. | |
| 6,930,602 | B2 * | 8/2005 | Villaseca | H01Q 1/2266 128/903 |
| 7,149,581 | B2 * | 12/2006 | Goedeke | A61B 5/0031 607/30 |
| 7,363,087 | B2 | 4/2008 | Nghiem et al. | |
| 7,392,092 | B2 * | 6/2008 | Li | A61N 1/37223 607/32 |
| 7,610,065 | B2 * | 10/2009 | Vallapureddy | A61N 1/37223 455/550.1 |
| 7,672,731 | B2 * | 3/2010 | Dublin | A61N 1/37223 607/36 |
| 7,859,468 | B2 | 12/2010 | Ali et al. | |
| 8,259,005 | B1 * | 9/2012 | Lam | H01P 1/184 342/157 |
| 8,442,248 | B2 | 5/2013 | Solum | |
| 9,215,980 | B2 * | 12/2015 | Tran | A61B 5/0006 |

(Continued)

*Primary Examiner* — Kennedy Schaetzle
(74) *Attorney, Agent, or Firm* — Haynes and Boone, LLP; Eric Q. Li

(57) ABSTRACT

The present disclosure involves a method of communicating with an implantable medical device. A programmer is provided. The programmer has a plurality of diversity antennas. The diversity antennas are configured to send wireless signals to the implantable medical device. A subset of the diversity antennas is selected. A communications link is established between the programmer and the implantable medical device through the selected subset of the diversity antennas. A link quality of the communications link is measured. A different subset of the diversity antennas is selected to communicate with the implantable medical device if the link quality falls below a predetermined threshold.

20 Claims, 13 Drawing Sheets

(56) References Cited

U.S. PATENT DOCUMENTS

| | | | |
|---|---|---|---|
| 2006/0122665 A1* | 6/2006 | Nghiem | A61N 1/37229 607/60 |
| 2006/0194615 A1* | 8/2006 | Vallapureddy | A61N 1/37223 455/562.1 |
| 2007/0002961 A1* | 1/2007 | Hoctor | H04B 7/0857 375/267 |
| 2007/0213598 A1* | 9/2007 | Howard | A61M 5/142 600/300 |
| 2007/0288066 A1* | 12/2007 | Christman | A61N 1/37229 607/60 |
| 2008/0027501 A1 | 1/2008 | Haubrich et al. | |
| 2008/0089442 A1* | 4/2008 | Lee | H04B 7/0682 375/299 |
| 2008/0228237 A1 | 9/2008 | Bange et al. | |
| 2008/0288024 A1* | 11/2008 | Abrahamson | A61N 1/37223 607/60 |
| 2009/0132008 A1* | 5/2009 | Snitting | A61B 5/0031 607/60 |
| 2009/0270948 A1* | 10/2009 | Nghiem | A61N 1/37229 607/60 |
| 2010/0194647 A1* | 8/2010 | Man | H01Q 1/243 343/702 |
| 2011/0103273 A1* | 5/2011 | Dutta | H04B 7/0608 370/281 |
| 2011/0199915 A1* | 8/2011 | Santhanam | H04W 68/00 370/252 |
| 2013/0095874 A1* | 4/2013 | Moshfeghi | H04W 88/06 455/509 |

* cited by examiner

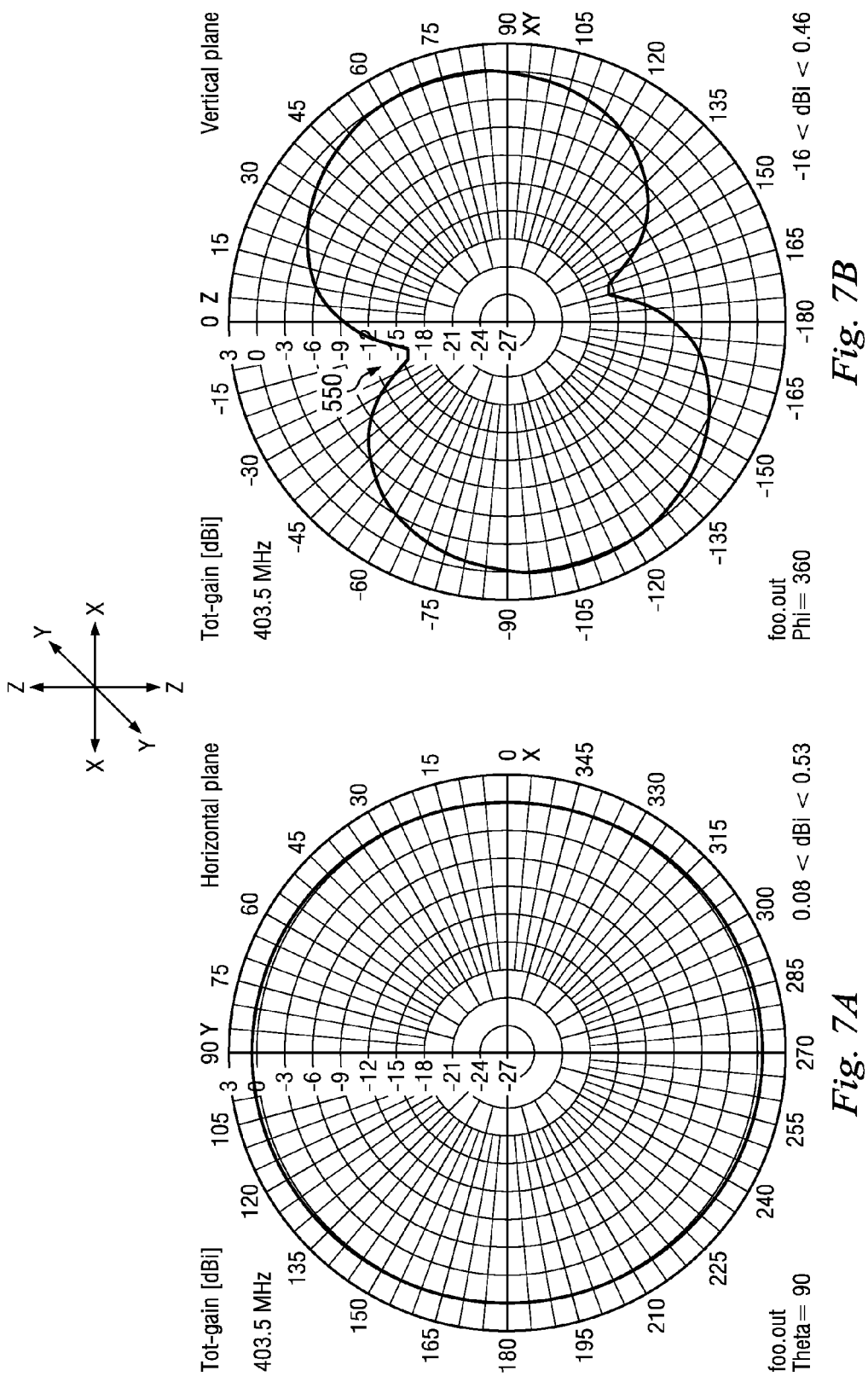

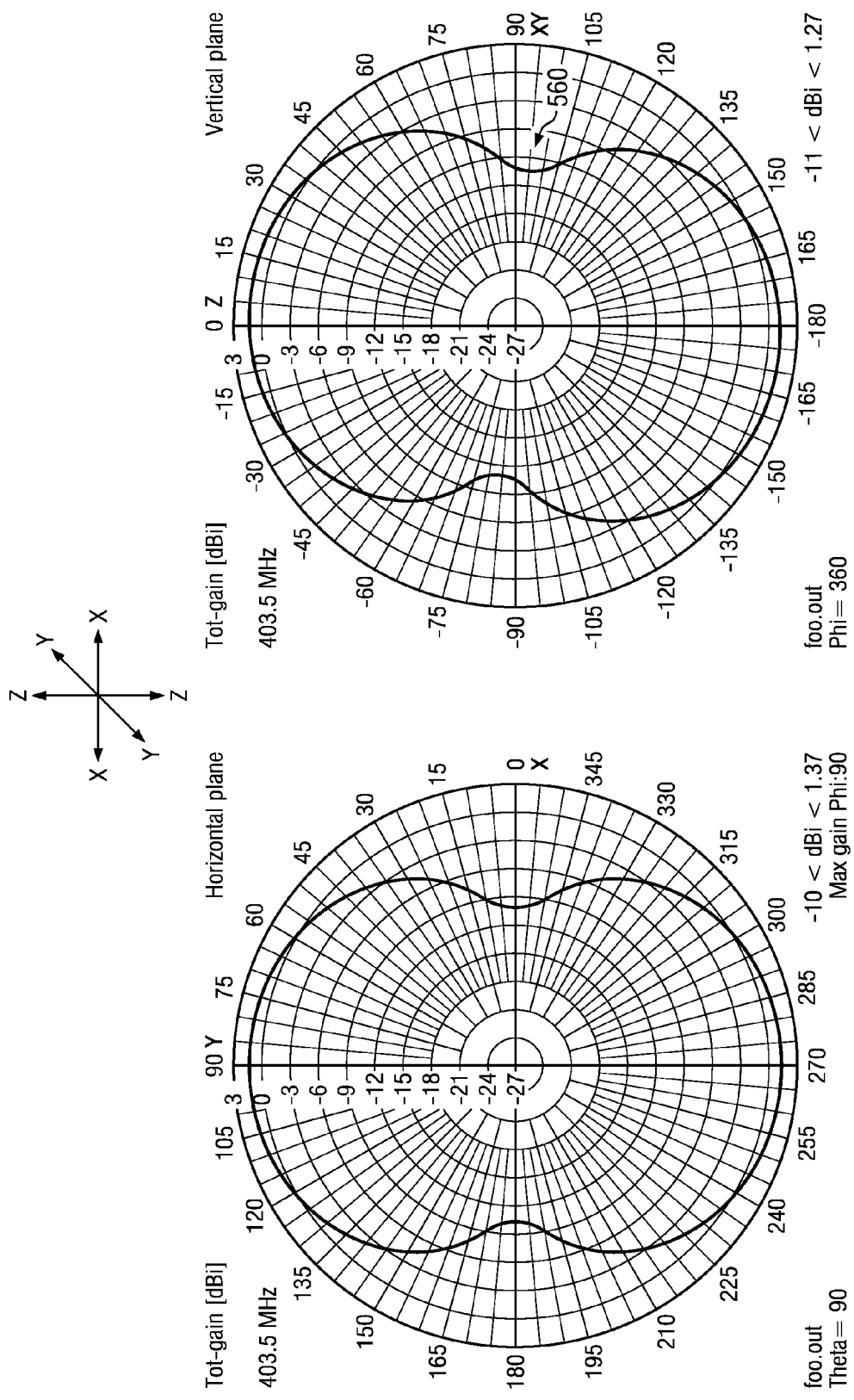

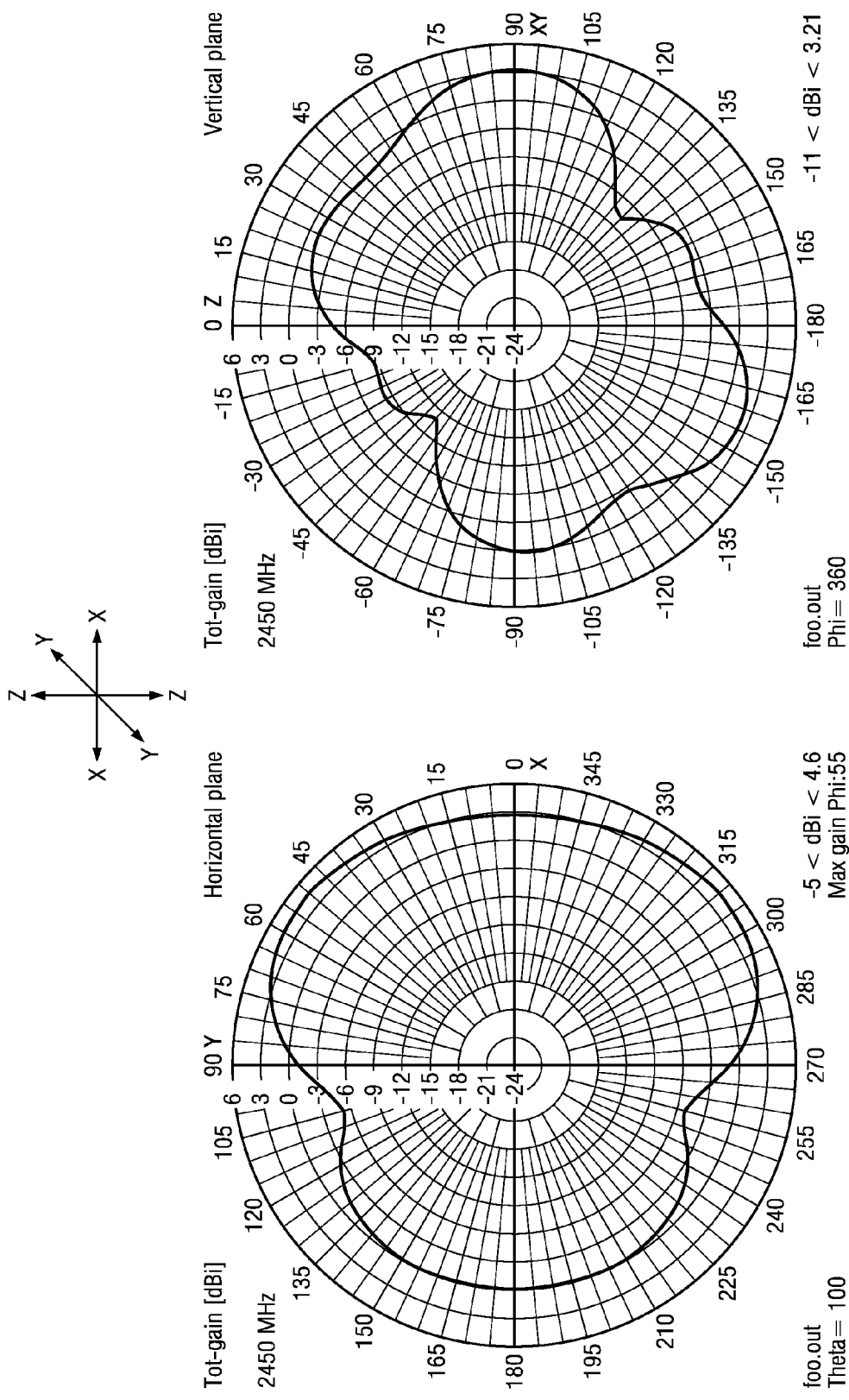

DIVERSITY ANTENNAS FOR NEUROSTIMULATOR PROGRAMMING DEVICES

PRIORITY DATA

The present application is a divisional application of U.S. patent application Ser. No. 13/442,283, filed on Apr. 9, 2012, entitled "Diversity Antennas for Neurostimulator Programming Devices", now U.S. Pat. No. 9,002,466 issued Apr. 7, 2015, the disclosure of which is hereby incorporated by reference in its entirety.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients.

An implanted medical device (for example a neurostimulator) can be controlled using an electronic programming device such as a clinician programmer or a patient programmer. These programmers can be used by medical personnel or the patient to define the particular electrical stimulation therapy to be delivered to a target area of the patient's body or alter one or more parameters of the electrical stimulation therapy. Advances in the medical device field have improved the electronic programmers. However, existing electronic programmers may still have shortcomings such as unreliable communication with the implanted medical devices. The communication difficulties may be exacerbated as the required communication distance becomes greater, or when the programmer has to operate in an electronically noisy environment. Unreliable communication problems may interfere with the intended operation of the implanted medical device and may hurt the clinician's or the patient's perception of the programmer, thereby limiting its adoption and use.

Therefore, although electronic programming devices for controlling implanted medical devices have been generally adequate for their intended purposes, they have not been entirely satisfactory in every aspect.

SUMMARY

One of the broader forms of the present disclosure involves a programmer configured to program an implanted medical device. The programmer includes: a circuit board; a first wireless communication device located on the circuit board, the first wireless communication device being configured to operate in a first frequency band; a second wireless communication device located on the circuit board, the second wireless communication device being configured to operate in a second frequency band that is different from the first frequency band, wherein the first wireless communication device and the second wireless communication device are each configured to communicate wirelessly with the implanted medical device; a first group of antennas coupled to the first wireless communication device, wherein the antennas in the first group have first different positions on the circuit board; and a second group of antennas coupled to the second wireless communication device, wherein the antennas in the second group have second different positions on the circuit board.

Another one of the broader forms of the present disclosure involves a medical system. The medical system includes: an implantable medical device; and a controller configured to send wireless programming signals to the implantable medical device, the controller including an electronic circuit board on which a plurality of electronic components is implemented, wherein the electronic components include: a first wireless communication device configured to operate in a first frequency band; a first set of antennas coupled to the first wireless communication device and dedicated to the first frequency band, the first set of antennas having first diverse locations on the electronic circuit board; a second wireless communication device configured to operate in a second frequency band different from the first frequency band; and a second set of antennas coupled to the second wireless communication device and dedicated to the second frequency band, the second set of antennas having second diverse locations on the electronic circuit board.

Yet another one of the broader forms of the present disclosure involves an apparatus for controlling an implanted medical device. The apparatus includes: a first communications means for performing electronic communication in a first frequency band with the implanted medical device; a plurality of first diversity antennas for transmitting or receiving signals between the first communications means and the implanted medical device; a second communications means for performing electronic communication in a second frequency band with the implanted medical device; and a plurality of second diversity antennas for transmitting or receiving signals between the second communications means and the implanted medical device; wherein: the first diversity antennas have first diverse radiation patterns from one another; and the second diversity antennas have second diverse radiation patterns from one another.

One more of the broader forms of the present disclosure involve a method of communicating with an implantable medical device. The method includes: providing a programmer having a plurality of diversity antennas, the diversity antennas being configured to send wireless signals to the implantable medical device; selecting a subset of the diversity antennas; establishing a communications link between the programmer and the implantable medical device through the selected subset of the diversity antennas; measuring a link quality of the communications link; and repeating the establishing the communications link at least in part by using a different subset of the diversity antennas if the link quality falls below a predetermined threshold.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIGS. 7A-7D are radiation patterns corresponding to a main transceiver of the programmer of FIG. 3.

FIGS. 8A-8D are radiation patterns corresponding to a wakeup transmitter of the programmer of FIG. 3.

DETAILED DESCRIPTION

Figure 1:
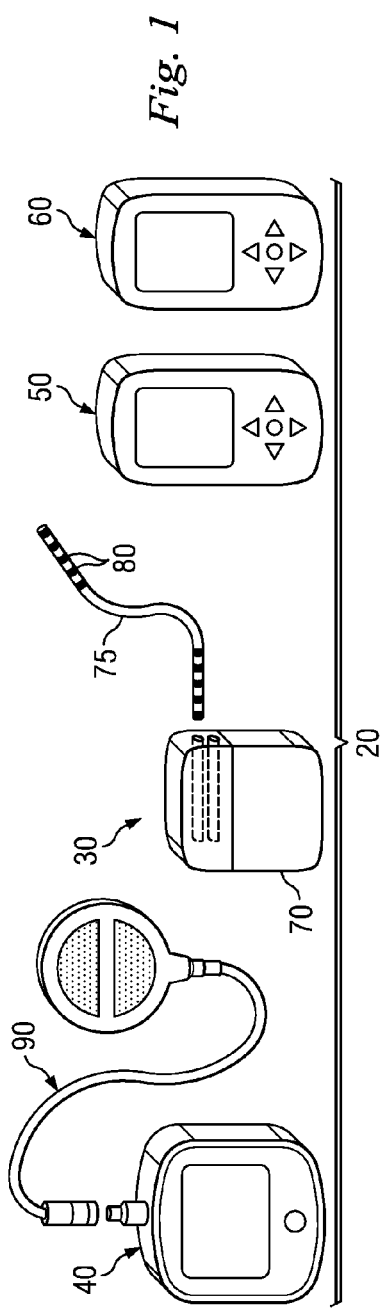
FIG. 1 is a simplified diagrammatic view of an embodiment of a medical system.

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Electronic programmers have been used to configure or program active implanted medical devices such as neurostimulators so that they can be operated in a certain manner. These electronic programmers include clinician programmers and patient programmers, each of which may be a handheld device. A clinician programmer allows a medical personnel (e.g., a doctor or a nurse) to define the particular electrical stimulation therapy to be delivered to a target area of the patient's body, while a patient programmer allows a patient to alter one or more parameters of the electrical stimulation therapy.

Over the years, these electronic programmers have achieved significant improvements, for example, improvements in size, power consumption, lifetime, and ease of use. However, existing programmers in the medical field may still have drawbacks. One such drawback is the lack of reliable and robust communication between the programmers and the implanted medical device. For example, the market demands reliable electronic communication between programmers and implanted medical devices over as great a distance as feasible. For the clinician, reliable communication is needed in order to quickly and efficiently configure the implanted medical device. For the patient, unreliable communication is perceived as an unreliable medical system, while medical devices should always be, and be seen as, reliable.

A number of factors conspire against reliability, however: Radio-Frequency (RF) power output is limited by regulation; antenna performance is limited by a market pressure to make small and sleek implanted medical devices and programmers, which limits antenna size and configuration; passing through body tissue attenuates the RF signal sent to or from an implanted medical device; and the environments in which these devices are used, particularly in hospitals and medical offices, are full of metal objects that reflect radio waves and lead to multipath fading.

Meanwhile, in many cases, the patient needs the patient programmer to communicate reliably with an implanted medical device up to a distance of approximately one meter, and the clinician programmer needs to communicate reliably with an implanted medical device at a distance of two meters or more. In addition, the environment surrounding the programmers is unpredictable. Holding a programmer in the wrong way can directly attenuate the RF signal from one or more antennas and can also detune one or more antennas, causing them to radiate less power. Furthermore, the environment varies widely. The nature of multipath fading and the ultra-high frequency (UHF) and microwave frequencies used in this system means that moving an antenna even a few inches may cause either a fade with high attenuation or summing that increases the power received. Reliable communications within the specified ranges requires preventing loss of communications from fading and/or hand effects.

To overcome these problems facing the existing electronic programmers, antenna diversity is utilized in a medical device programmer according to various aspects of the present disclosure.

Referring to FIG. 1, a simplified block diagram of an implanted medical device system 20 is illustrated. The implanted medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end of one or more percutaneous, or skin-penetrating, leads. The other end of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 of the medical device system 20 is used by a patient in whom the IPG 70 is implanted. The patient may adjust the parameters of the stimulation, such as by selecting a program, changing its amplitude, frequency, and other parameters, and by turning stimulation on and off. The clinician programmer 60 of the medical device system 20 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

Figure 2:
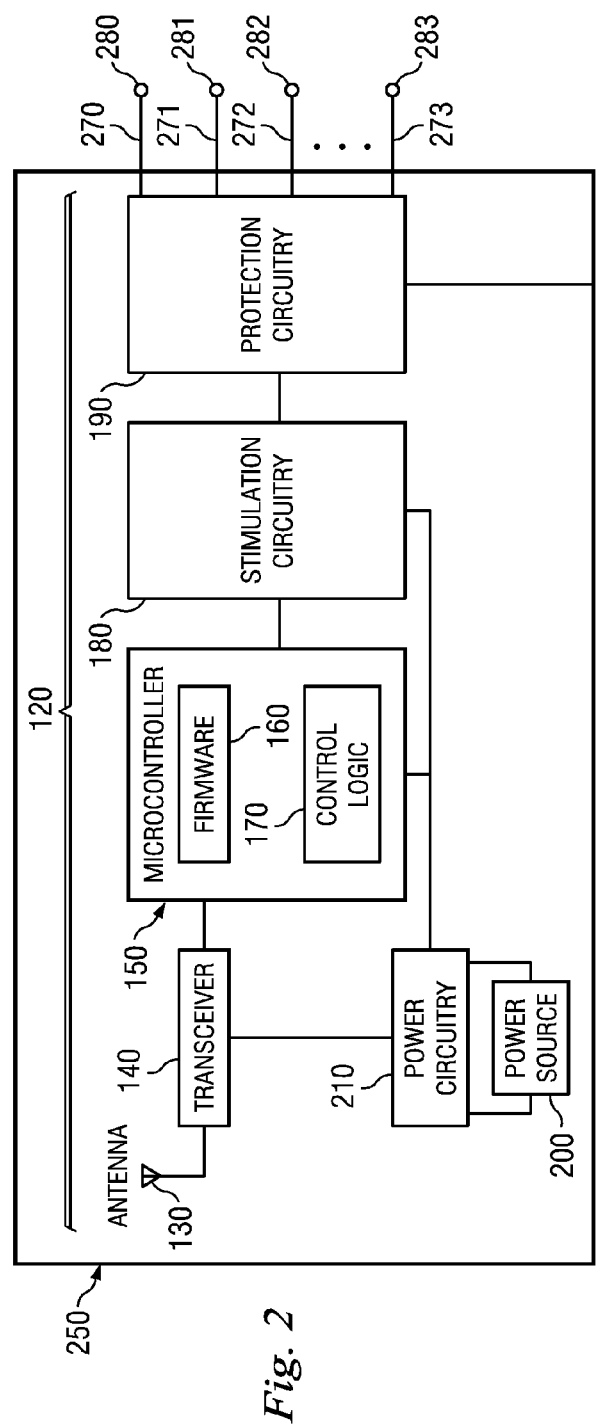
FIG. 2 is a simplified diagrammatic view of an embodiment of an implanted medical device.

FIG. 2 is a simplified diagrammatic view of an example of a neurostimulator device 120 as an embodiment of the implantable medical device 30. The neurostimulator device 120 includes an antenna 130 and a transceiver 140 coupled to the antenna 130. The antenna 130 is capable of sending signals to an external device and receiving signals from the external device. The transceiver 140 contains transmitter circuitry and receiver circuitry that together carry out digital communication with the external device. In an embodiment, the signals are transmitted and received at Radio Frequencies (RF).

The neurostimulator device 120 includes a microcontroller 150 that is coupled to the transceiver 140. Based on the output of the transceiver 140 (i.e., the input received from the external device), the microcontroller 150 runs firmware 160, which is a control program, to operate control logic 170. The firmware 160 includes dedicated low-level software code that is written for a specific device, in this case the control logic 170. The control logic 170 includes digital circuitry that is implemented using a plurality of transistors, for example Field Effect Transistors (FETs). In the embodiment shown in FIG. 2, the firmware 160 and the control logic 170 are integrated into the microcontroller 150. In alternative embodiments, the firmware 160 or the control logic 170 may be implemented separately from the microcontroller 150.

The neurostimulator device 120 includes stimulation circuitry 180 that receives the output of the microcontroller 150. In an embodiment, the stimulation circuitry 180 is implemented on an Application Specific Integrated Circuit (ASIC) chip. The stimulation circuitry 180 includes electrical pulse generation circuitry. Based on the output of the microcontroller 150, the electrical pulse generation circuitry generates electrical pulses (signals) to a target tissue area. Various aspects of the pulse generation are described in detail in U.S. patent application Ser. No. 13/081,896, Titled "Charge Balancing For Arbitrary Waveform Generator & Neural Stimulation Application" and filed on Apr. 7, 2011, U.S. patent application Ser. No. 13/082,097, Titled "Arbitrary Waveform Generator & Neural Stimulation Application With Scalable Waveform Feature" and filed on Apr. 7, 2011, and U.S. patent application Ser. No. 13/081,936, Titled "Arbitrary Waveform Generator & Neural Stimulation Application" and filed on Apr. 7, 2011, each of which is hereby incorporated by reference in its entirety. Other aspects of the stimulation circuitry 180 will be discussed later in greater detail.

The neurostimulator device 120 also includes protection circuitry 190 that is coupled to the output of the stimulation circuitry 180. In an embodiment, the protection circuitry 190 includes direct-current (DC) blocking capacitors and other electrical transient suppression components. The protection circuitry 190 protects the patient's tissue from unwanted electrical signals. The protection circuitry 190 also protects the neurostimulator device 120 from undesirable external events such as electrostatic discharge, defibrillation, or electrocautery.

The neurostimulator device 120 also includes a power source 200 and power circuitry 210. In an embodiment, the power source 200 includes a battery. In another embodiment, the power source 200 includes a coil that is a part of a transformer (not illustrated). In that case, the transformer has a charging coil that is external to the neurostimulator device 120 and inductively coupled to the coil of the power source 200. The power source 200 therefore obtains energy from such inductive coupling to the charging coil. In some embodiments, the power source 200 may also include both a battery and a coil. The power source 200 provides electrical power to the power circuitry 210. The power circuitry 210 is coupled to the transceiver 140, the microcontroller 150, and the stimulation circuitry 180. The power circuitry 210 supplies and regulates power to these coupled circuitries. In an embodiment, the power circuitry 210 is implemented on an ASIC device.

In an embodiment, the antenna 130, the transceiver 140, the microcontroller 150, the stimulation circuitry 180, the protection circuitry 190, the power source 200, and the power circuitry 210 may be collectively viewed as a stimulation circuit (or components of the stimulation circuit) and are all contained within a hermetically-sealed enclosure 250 (which may also be referred to as a can or a housing). The enclosure 250 may also be considered a part of the neurostimulator device 120. The enclosure 250 may be made from titanium or another suitable biocompatible, durable, and/or conductive material. According to various aspects of the present disclosure, the enclosure 250 is also electrically coupled to the stimulation circuitry 180 through the protection circuitry 190, in a manner such that the stimulation circuitry can drive the enclosure 250 with an electrical supply such as a current sink or a current source.

A plurality of conductors run from the internal circuitry through hermetic feedthroughs to one or more connectors (also referred to as headers) mounted on the enclosure 250. The lead wires 270-273 plug into, and are removable from, those connectors. In another embodiment, the connectors are eliminated, and the lead wires 270-273 are directly and permanently connected to the hermetic feedthroughs. In some embodiments, the neurostimulator device 120 incorporates the electrode contacts (such as the electrode contacts 280-283 discussed below) into its outer surface. In such embodiments, the hermetic feedthroughs may be designed to incorporate an electrode contact in the tissue-facing side of each feedthrough, or may be designed to have insulated lead wires built into the neurostimulator housing, exterior to the hermetically-sealed enclosure 250, that carry signals between the hermetic feedthroughs and the electrode contacts. It is understood that the lead wires 270-273 are shown merely as examples, and that an alternative number of lead wires may be implemented, for example 16 or 24 lead wires.

Electrode contacts 280-283 (also referred to as electrodes) are coupled to the lead wires 270-273. The electrode contacts 280-283 are implanted in different areas of a patient's body, where electrical stimulation is desired. According to various aspects of the present disclosure, an exterior conductive portion of the enclosure 250 is also used as an electrode contact. This will be discussed in more detail below. In any case, the electrode contacts 280-283 may also be considered parts of the neurostimulator system.

In an embodiment, the neurostimulator device 120 is implemented as an Implanted Pulse Generator (IPG) device, in which case all of the components shown in FIG. 2 are surgically implanted inside the patient's body. A medical device manufacturer may manufacture and provide the neurostimulator device 120 to a clinician or a patient. Clinicians may also provide the neurostimulator device to a patient. Some of the functionalities of the microcontroller 150 may be pre-programmed by the manufacturer or may be programmed by the clinician or patient. It is understood that the neurostimulator 120 described above is merely an example of an implanted medical device, and that other types of implanted medical devices may be implanted inside a patient's body and be controlled by clinician or patient programmers.

Various aspects of the programmer for controlling the implanted medical device (such as the neurostimulator 120) will now be described.

Figure 3:
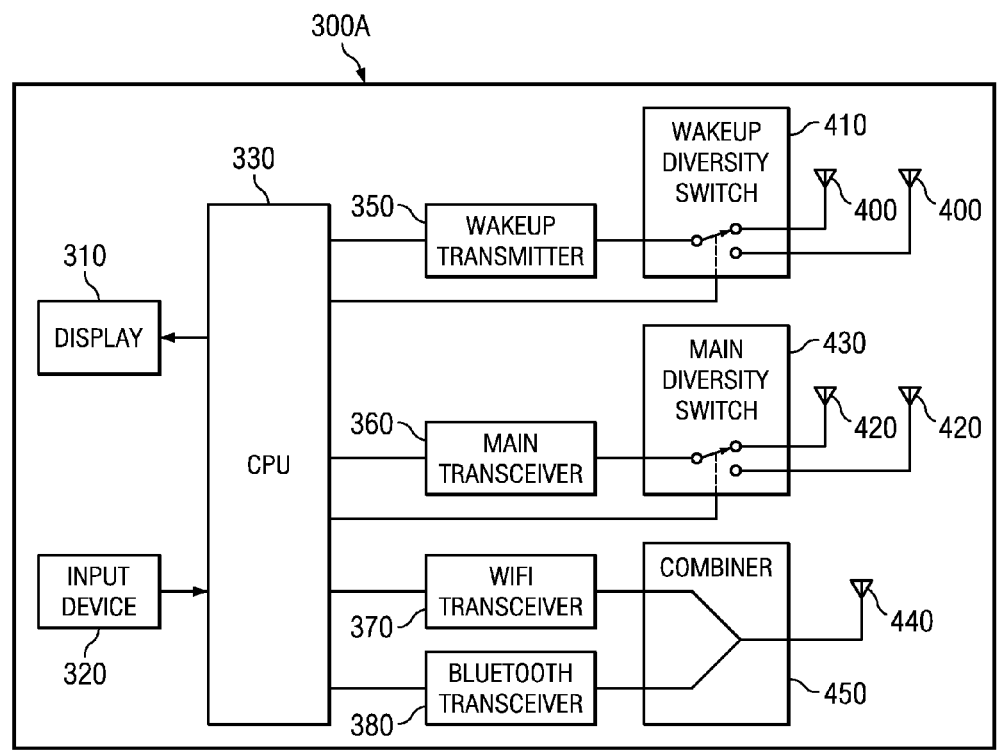
FIG. 3 is a simplified diagrammatic view of an embodiment of a programmer for controlling the implanted medical device of FIG. 2.

FIG. 3 is a simplified diagrammatic view of an embodiment of a medical device programmer 300A that can be used as the patient programmer 50 or the clinician programmer 60 of FIG. 1. The programmer 300A includes a display 310, an input device 320, and a central processing unit (CPU) 330. The display 310 is operable to present information to the user of the programmer 300A. In some embodiments, the display 310 includes a graphical screen. The input device 320 is operable to receive commands from the user. In some embodiments, the input device 320 includes a touch-sensitive screen and/or one or more buttons. In some other embodiments, the input device 320 may include a mouse, a trackball, a touchpad, a keyboard, a stylus, an accelerometer, a voice recognition mechanism, or another suitable device. The display 310 and the input device 320 are each coupled to the CPU 330. The CPU 330 is operable to execute tasks based on the commands given by the user of the programmer 300A through the input device 320. The CPU 330 is also operable to feed information back to the user through the display 310. Among other things, the CPU 330 includes a microprocessor, firmware, data storage, and interface circuitry.

To communicate with an implanted medical device (such as the neurostimulator device 120 of FIG. 2), the programmer 300A also includes a plurality of wireless communication devices. The wireless communication devices may include wireless transmitters, wireless receivers, wireless transceivers, or other suitable devices capable of conducting wireless communication with external devices. In the illustrated embodiment, the wireless communication devices include a wakeup transmitter 350, a main transceiver 360, a WiFi transceiver 370, and a Bluetooth transceiver 380. The wakeup transmitter 350 operates in the 2.45 Giga Hertz (GHz) unlicensed band. In alternative embodiments, a wakeup transceiver (i.e., a wireless communication device having both transmit and receive capabilities) may be implemented in place of the wakeup transmitter. The main transceiver 360 operates in the 403.5 Mega Hertz (MHz) MedRadio band, which is also known as the Medical Implant Communications Service, or MICS band.

In some embodiments, to begin communication with an implanted medical device that is in a "sleep" mode, the programmer 300A may first send wakeup packets to the medical device through the wakeup transmitter 350 over the 2.45 GHz band. These wakeup packets signal the implanted medical device to power up its main wireless communication device. Thereafter, the implanted medical device and the programmer may continue communications through the main transceiver 360 in the 403.5 MHz band.

The WiFi transceiver 370 and the Bluetooth transceiver 380 also each operate in the 2.45 GHz band. The WiFi transceiver 370 and the Bluetooth transceiver 380 offer the programmer 300A greater communications capabilities in communicating with the implanted medical device, as they employ alternative means (and protocols) of communication. The WiFi transceiver 370 is implemented in accordance with the IEEE 802.11 standard, and the Bluetooth transceiver 380 is implemented in accordance with the IEEE 802.15 standard. In some embodiments, the WiFi transceiver 370 and the Bluetooth transceiver 380 are optional. It is understood that the CPU 330 may contain logic circuitry for controlling the operations of the wakeup transmitter 350, the main transceiver 360, the WiFi transceiver 370, and the Bluetooth transceiver 380.

The wakeup transmitter 350 is coupled to a plurality of diversity antennas 400 through a wakeup diversity switch 410, and the main transceiver 360 is coupled to a plurality of diversity antennas 420 through a main diversity switch 430. The wakeup diversity switch 410 is a double-throw switch that couples the wakeup transmitter 350 to one of the diversity antennas 400. In some embodiments, the wakeup diversity switch 410 is a Peregrine Semiconductor PE4242 device. The main diversity switch 430 is a double-throw switch that couples the main transceiver 360 to one of the diversity antennas 420. In some embodiments, the main diversity switch 430 is a Peregrine Semiconductor PE4210 device. The WiFi transceiver 370 and the Bluetooth transceiver 380 are both coupled to an antenna 440 through a power combiner 450. Thus, the single antenna 440 can be used as the antenna for both the WiFi transceiver 370 and the Bluetooth transceiver 380. It is also understood that the programmer 300A may include additional components or circuitry not illustrated herein. For example, the programmer 300A may include a battery and power management circuitry. The main transceiver 360 may also include a transmit/receive (T/R) switch for switching between a transmit path and a receive path. These additional components or circuitries are not specifically illustrated herein for reasons of simplicity.

Figure 4:
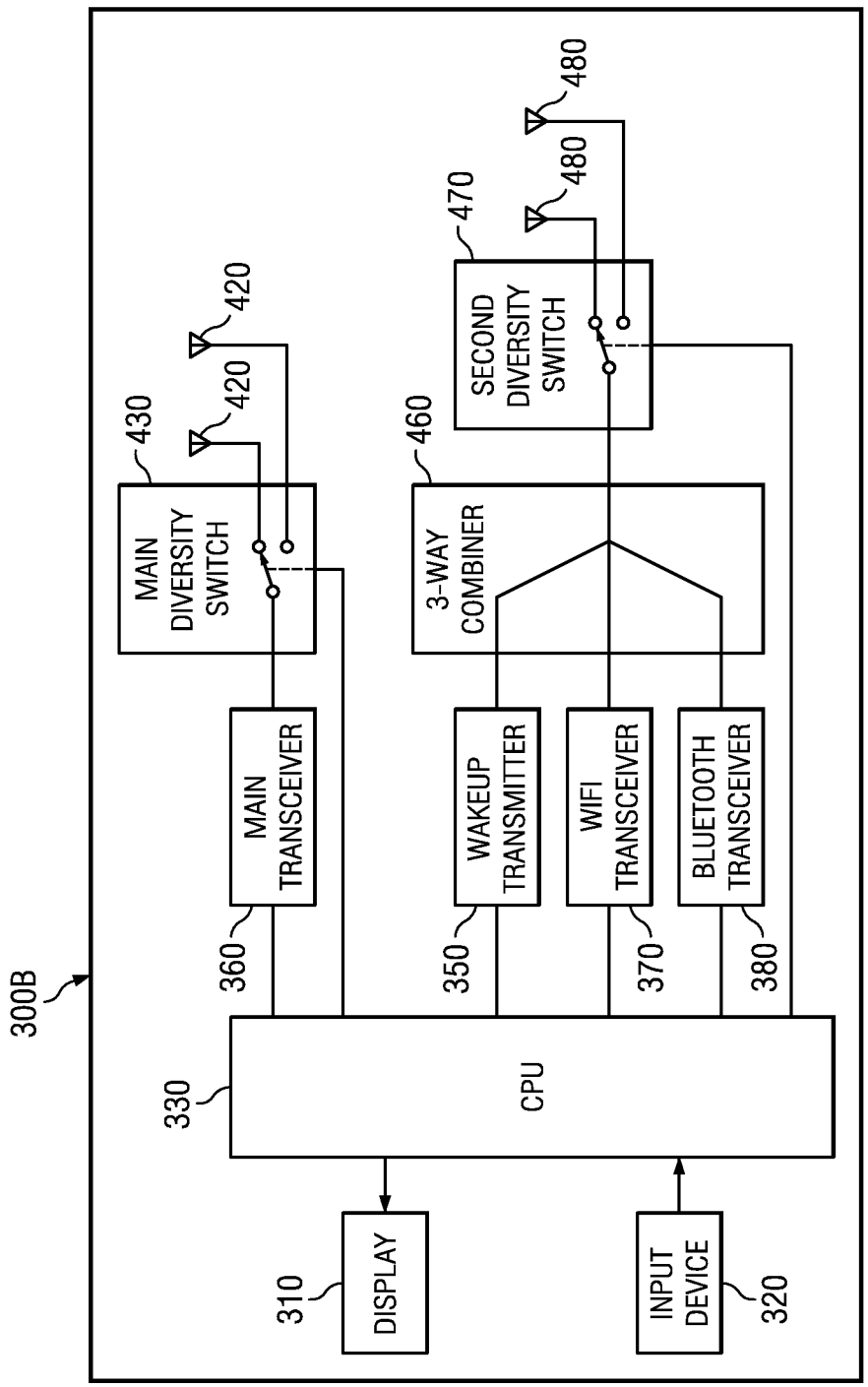
FIG. 4 is a simplified diagrammatic view of another embodiment of a programmer for controlling the implanted medical device of FIG. 2.

FIG. 4 is a simplified diagrammatic view of another embodiment of a medical device programmer 300B that can be used as the patient programmer 50 or the clinician programmer 60 of FIG. 1. The programmer 300B is similar to the programmer 300A in many aspects, and therefore similar components are labeled the same for both the programmers 300A and 300B for the sake of clarity and consistency.

Referring to FIG. 4, the programmer 300B includes the display 310, the input device 320, the CPU 330, the wakeup transmitter 350, the main transceiver 360, the WiFi transceiver 370, and the Bluetooth transceiver 380. The main transceiver 360 is coupled to the diversity antennas 420 through the main diversity switch 430. Unlike the programmer 300A, the wakeup transmitter 350, the WiFi transceiver 370, and the Bluetooth transceiver 380 are all coupled to a three-way power combiner 460. The power combiner 460 is coupled to a second diversity switch 470 that is similar to the main diversity switch 430. The second diversity switch 470 is coupled to a plurality of diversity antennas 480.

Compared to the programmer 300A of FIG. 3, the programmer 300B of FIG. 4 effectively eliminates a separate antenna (e.g., antenna 440 of FIG. 3) that was previously dedicated to the WiFi transceiver 370 and the Bluetooth transceiver 380. The reduced number of antennas may be beneficial if board or chip space is at a premium. Also, with suitable logic within the CPU 330 to set the diversity switch 470 in coordination with transmissions, time-division multiplexing may be implemented between the transceivers 350, 370, and 380 so that the antenna choice can be different for transmissions from each transceiver. Also, the three-way combiner 460 can be built with unequal losses for the three ports. Thus, the design of the programmer 300B offers a degree of design flexibility in allocating the loss of the combiner between the three transceivers 350, 370, and 380.

However, the three-way combiner 460 has higher loss than the two-way combiner 450 of the programmer 300A of FIG. 3. In addition, optimizing the logic of the CPU 330 to correctly perform the time-division multiplexing discussed above increases design complexity. Therefore, the programmers 300A and 300B involve various tradeoffs including performance, space, and design and implementation complexity. It is understood that the designs shown in FIGS. 3-4 are not intended to be limiting, and that additional tweaks to the design may be made to optimize any particular area of concern.

The details of the diversity antennas (e.g., the diversity antennas 400, 420, and 480) will now be discussed according to various aspects of the present disclosure.

Figure 5:
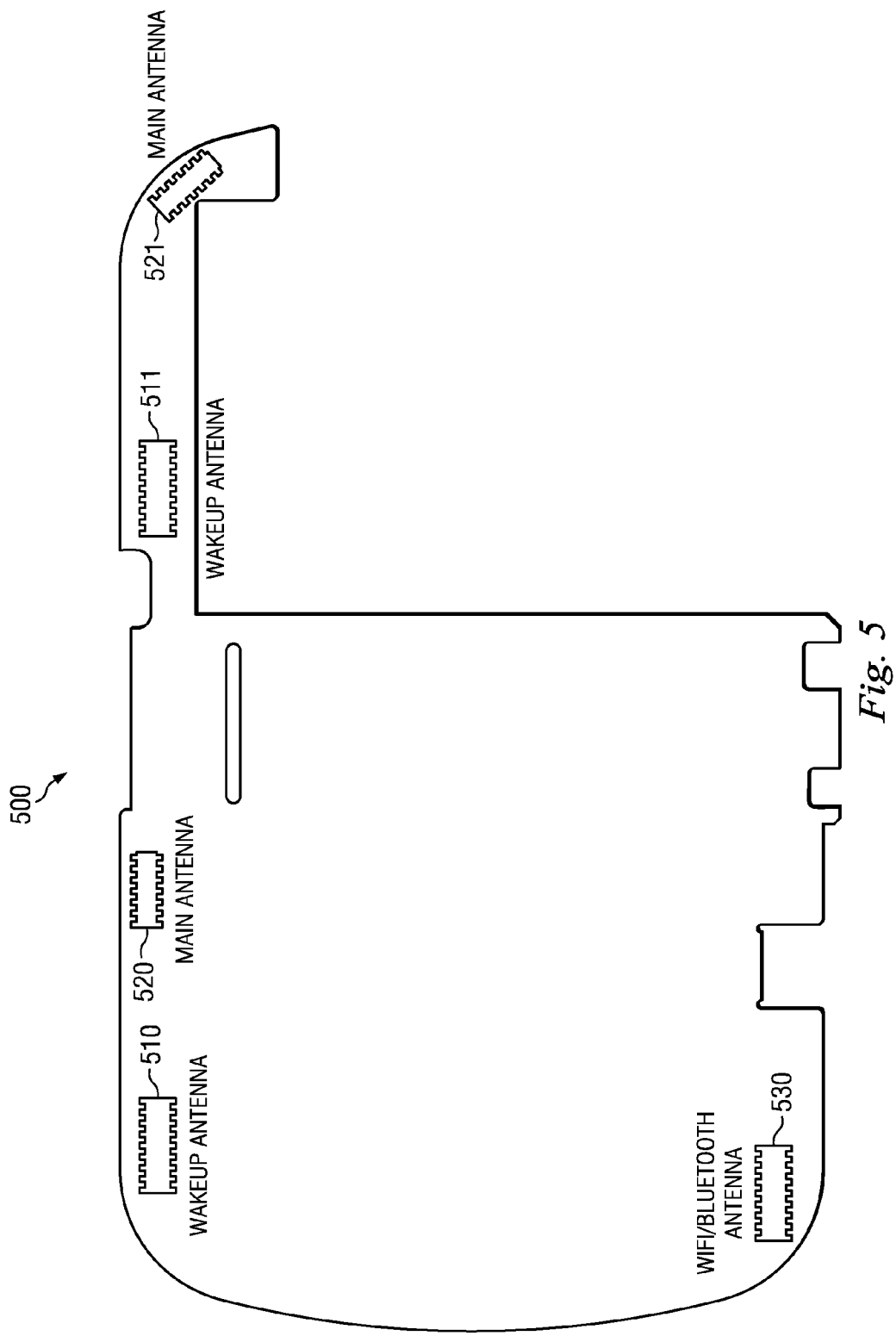
FIG. 5 is a simplified top view of a circuit board of the programmer of FIG. 3 having a plurality of diversity antennas located thereon.

Referring to FIG. 5, a simplified diagrammatic top view of a circuit board 500 of a programmer is illustrated according to an embodiment of the present disclosure. Among other things, wakeup antennas 510-511 are implemented on the circuit board 500 as the diversity antennas 400 for the wakeup transmitter 350 shown in FIG. 3, and main antennas 520-521 are implemented on the circuit board 500 as the diversity antennas 420 for the main transceiver 360 shown in FIG. 3. A WiFi/Bluetooth antenna 530 is also implemented on the circuit board 500 as the antenna 440 for the WiFi transceiver 370 and the Bluetooth transceiver 380 shown in FIG. 3. Various other electronic components of the programmer discussed above may be implemented on the circuit board 500, but they are not illustrated herein for reasons of simplicity.

As is shown in FIG. 5, the two wakeup antennas 510-511 are spread across the top edge of the circuit board 500, and the two main antennas 520-521 are also spread across the top edge of the circuit board 500. The two wakeup antennas 510-511 have first diverse locations from one another, and the two main antennas 520-521 have second diverse locations from one another. The first diverse locations of the wakeup antennas 510-511 (and the second diverse locations of the main antennas 520-521) are configured to enhance signal reception. In more detail, the wakeup antennas 510-511 are dedicated to the wakeup transmitter 350, which operates in the 2.45 GHz band, whereas the main antennas 520-521 are dedicated to the main transceiver 360, which operates in the 403.5 MHz band. Both of these bands are at relatively high frequencies, and therefore have small corresponding wavelengths. The small wavelengths mean that the antennas 510-511 and 520-521 are sensitive to movement or positional displacement. In other words, a small change in the location of one of these antennas may lead to a significant change in its signal pattern. Therefore, having two (or more) antennas physically spaced apart from one another will minimize the likelihood of both antennas having bad reception. Hence, even if one of the two (or more) antennas experiences bad signal reception, the other antenna(s) may still have good enough signal reception, thereby allowing the corresponding wireless communication device to function properly. Thus, the embodiments of the present disclosure utilize spatial diversity for its antennas to improve the wireless communication.

In addition, since the bands for the wakeup transmitter 350 and the main transceiver 360 are quite different, wireless signals for these two bands have significantly different wavelengths too. Consequently, multipath fading will affect these two bands very differently. An interference signal for one band may not be an interference signal for the other band. In that regard, the embodiments of the present disclosure may also utilize frequency diversity for its antennas to improve the wireless communication.

Furthermore, as is shown in FIG. 5, the circuit board 500 is asymmetrical. Stated differently, the left half of the circuit board 500 is substantially greater (or more "filled out") than the right half of the circuit board. In some embodiments, a battery may be implemented in place of the "missing" right half of the circuit board 500. Due to the asymmetry of the circuit board 500, the wakeup antennas 510-511 have different distances and angles to the effective "center" of the circuit board 500. The same is true for the main antennas 520-521. These different distances and angles will also lead to pattern diversity for the wakeup antennas 510-511, as well as pattern diversity for the main antennas 520-521, which further enhances antenna reception quality. Though not illustrated herein, additional asymmetry may be achieved by orienting the antennas differently. As an example, the wakeup antenna 510 and the main antenna 520 may be oriented horizontally (as they are in FIG. 5), but the wakeup antenna 511 and the main antenna 521 may be oriented vertically.

Moreover, the locations of the wakeup antennas 510-511 and the main antennas 520-521 are chosen such that a single hand (e.g., hand of a human operator) holding the programmer is unlikely to cover or detune both of the wakeup antennas 510-511 simultaneously, or both of the main antennas 520-521 simultaneously, even though covering or detuning is quite possible for any single antenna. Therefore, by switching between wakeup antennas 510-511 and switching between the main antennas 520-521, the CPU 330 (shown in FIG. 3) can find the best antenna of each type for communicating with the desired implanted medical device.

In some embodiments, the wakeup antenna 510 may be physically different (e.g., with respect to physical characteristics such as size, shape, geometry, etc) from the wakeup antenna 511, and the main antenna 520 may be physically different from the main antenna 521. In some embodiments, the wakeup antennas 510-511 are physically substantially similar, as are the main antennas 520-521, but the wakeup antennas 510-511 are physically different from the main antennas 520-521. In other embodiments, each of the antennas 510-511 and 520-521 is different from the rest of the antennas in that group. These embodiments may further enhance antenna diversity and consequently optimize the signal reception.

In embodiments where the WiFi transceiver 370 and the Bluetooth transceiver 380 (FIG. 3) are implemented, the WiFi/Bluetooth antenna 530 is placed to be physically far apart from the wakeup antennas 510-511 and the main antennas 520-521, so as to minimize potential interference.

Figure 6A:
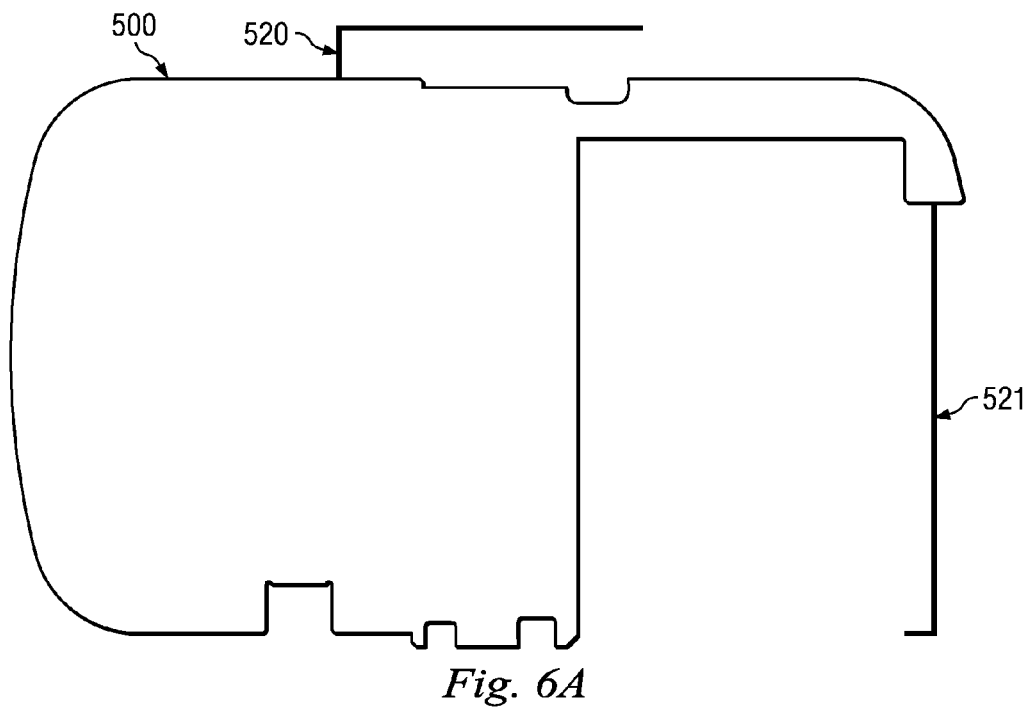
FIGS. 6A-6B are simplified top views of a circuit board of the programmer of FIG. 3 having a plurality of diversity antennas located thereon.
Figure 6B:
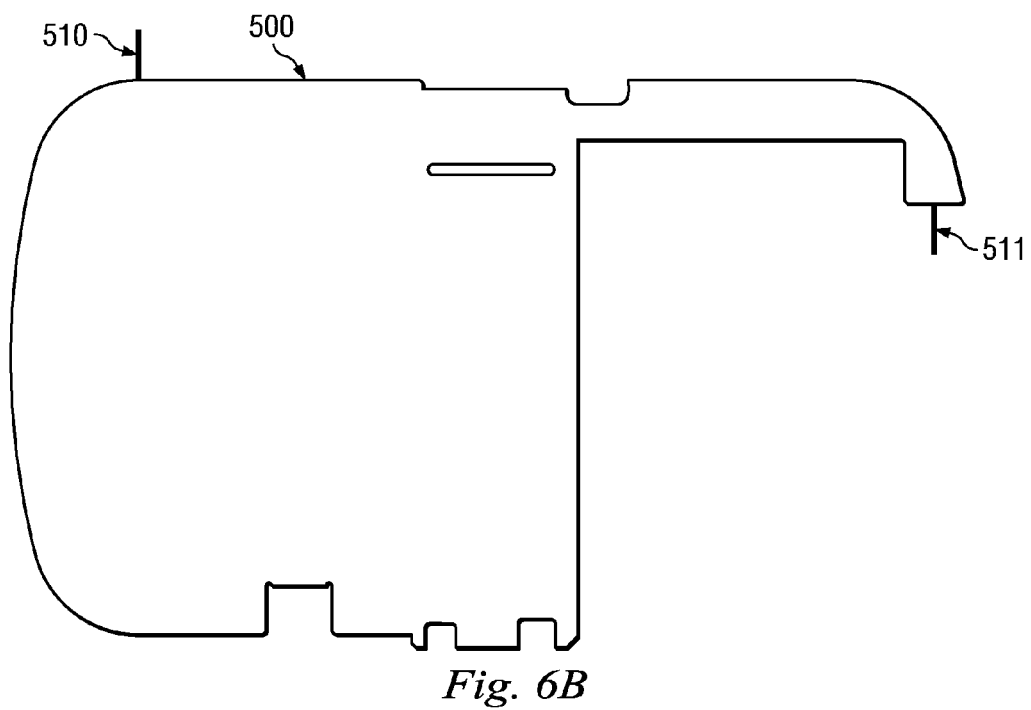

FIGS. 6A-6B illustrate simulated antenna patterns for the main antennas 520-521 to illustrate how pattern diversity is obtained by placing the antennas in different locations relative to the limited ground plane (of the circuit board) of the programmer. The simulation is performed where the circuit board 500 is situated in a vertical plane defined by an X axis and a Z axis. A horizontal plane defined by the X axis and a Y axis intersects with, and is orthogonal to, the vertical plane defined by the X and Z axes. The simulations were done using an embodiment of the programmer 300, whose simplified top view is shown in FIGS. 6A and 6B. Specifically, FIG. 6A shows a top view of the circuit board 500 and the main antennas 520-521, and FIG. 6B shows a top view of the circuit board 500 and the wakeup antennas 510-511. As is shown in FIG. 6A, the main antennas 520-521 are oriented differently from each other—the main antenna 520 mostly has a horizontal orientation, whereas the main antenna 521 mostly has a vertical orientation. Though the wakeup antennas 510-511 are both oriented in the vertical direction in the embodiment shown in FIG. 6B, they could have different orientations in other embodiments.

Based on the simulations performed based on the embodiments shown in FIGS. 6A-6B, the corresponding radiations patterns obtained are shown in FIGS. 7A-7D and 8A-8D. Specifically, FIG. 7A illustrates a radiation pattern of the main antenna 520 in the horizontal plane (defined by X and Y axes); FIG. 7B illustrates a radiation pattern of the main antenna 520 in the vertical plane (defined by the X and Z axes); FIG. 7C illustrates a radiation pattern of the main antenna 521 in the horizontal plane; and FIG. 7D illustrates a radiation pattern of the main antenna 521 in the vertical plane.

It can be seen that the main antenna 520 has a null 550 (shown in FIG. 7B) at about −15 degrees off the Z axis, while the main antenna 521 has a null 560 (shown in FIG. 7D) at about 5 degrees off the X axis. These differences in the nulls 550 and 560 mean that one antenna can be expected to have good gain in the direction of the other antenna's null. Therefore, it is possible to improve the range over which communications is possible by switching between the two antennas in a way that selects the most effective antenna for a given communication band.

Figures 8C, 8D:
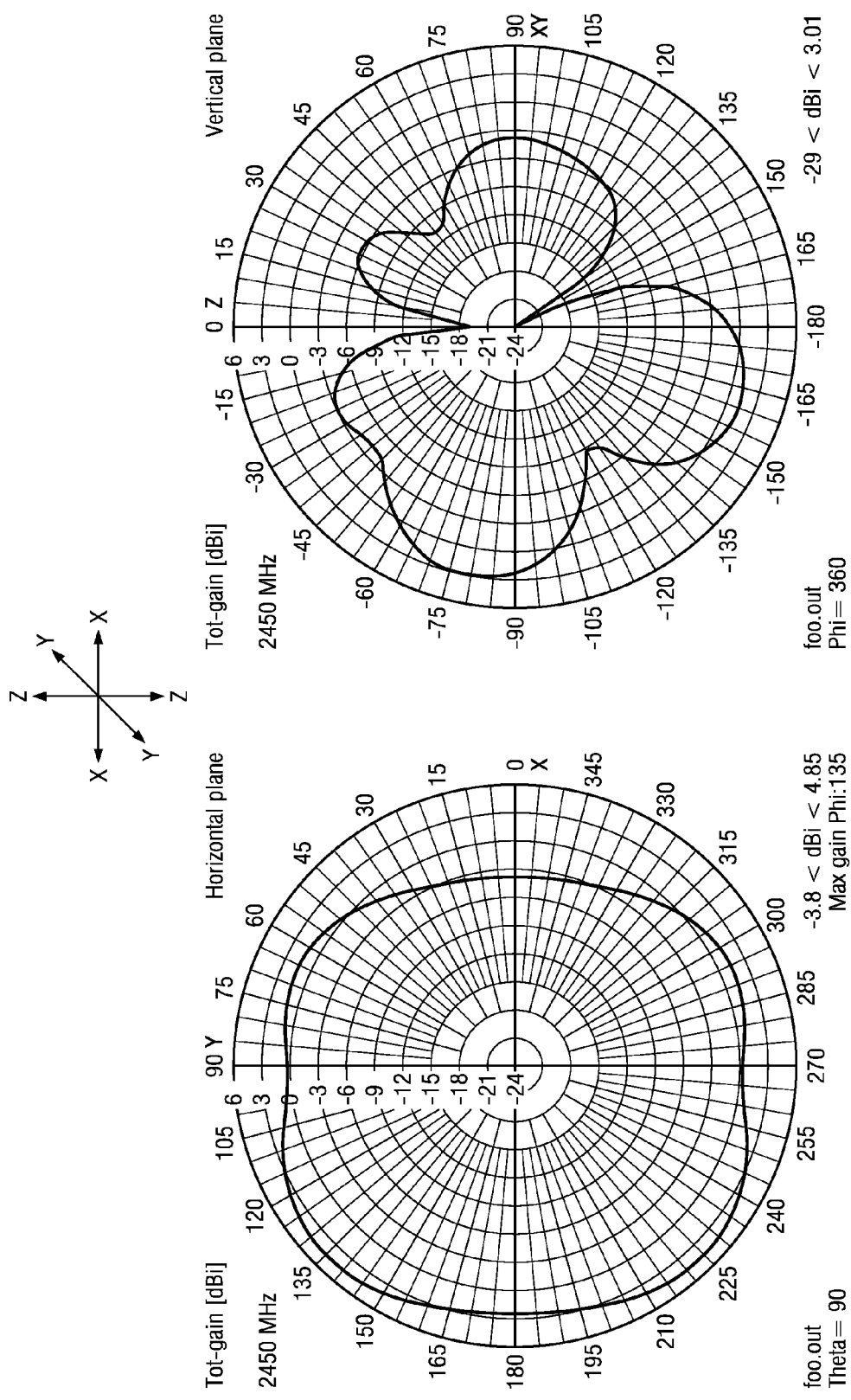

FIGS. 8A-8D illustrate simulated antenna patterns for the wakeup antennas 510-511 in a similar manner as FIGS. 7A-7D illustrate simulated antenna patterns for the main antennas 520-521. FIG. 8A illustrates a radiation pattern of the wakeup antenna 510 in the horizontal plane (defined by X and Y axes); FIG. 8B illustrates a radiation pattern of the wakeup antenna 510 in the vertical plane (defined by the X and Z axes); FIG. 8C illustrates a radiation pattern of the wakeup antenna 511 in the horizontal plane; and FIG. 8D illustrates a radiation pattern of the wakeup antenna 511 in the vertical plane. The patterns of the wakeup antennas 510-511 shown in FIGS. 8A-8D are more complex than those shown in FIGS. 7A-7D, particularly in the vertical plane. Nevertheless, it can be seen that the directions with lower gains on each antenna tend to have better gains on the other antenna. Hence, as with the main antennas 520-521, using the wakeup antennas 510-511 as a diversity pair can improve the range over which communication is possible.

It is understood that the radiation patterns illustrated in FIGS. 7A-7D and 8A-8D are merely simulation results based on simplified circuit board shapes (e.g., circuit board approximating the shape of the circuit board shown in FIGS. 6A-B) and are not intended to be limiting. Other radiation patterns similar to the radiation patterns shown in FIGS. 7A-7D and 8A-8D may be obtained by running simulations on modified circuit board shapes without departing from the scope and spirit of the present disclosure.

As discussed above, the programmer has multiple antennas (e.g., two) on each of the two frequency bands (e.g., the 2.45 GHz band and the 403.5 MHz band). Because of the different wavelengths, multipath fading will affect the two bands differently, and the antenna patterns on the two bands will be different. For these reasons, it is not practical to pair each wakeup antenna with one main antenna and choose between those two pairs of wakeup/main antennas. Instead, the wakeup and main antennas should be chosen separately, with four possible combinations: wakeup antenna 510 with main antenna 520; wakeup antenna 510 with main antenna 521; wakeup antenna 511 with main antenna 520; and wakeup antenna 511 with main antenna 521.

Figure 9:
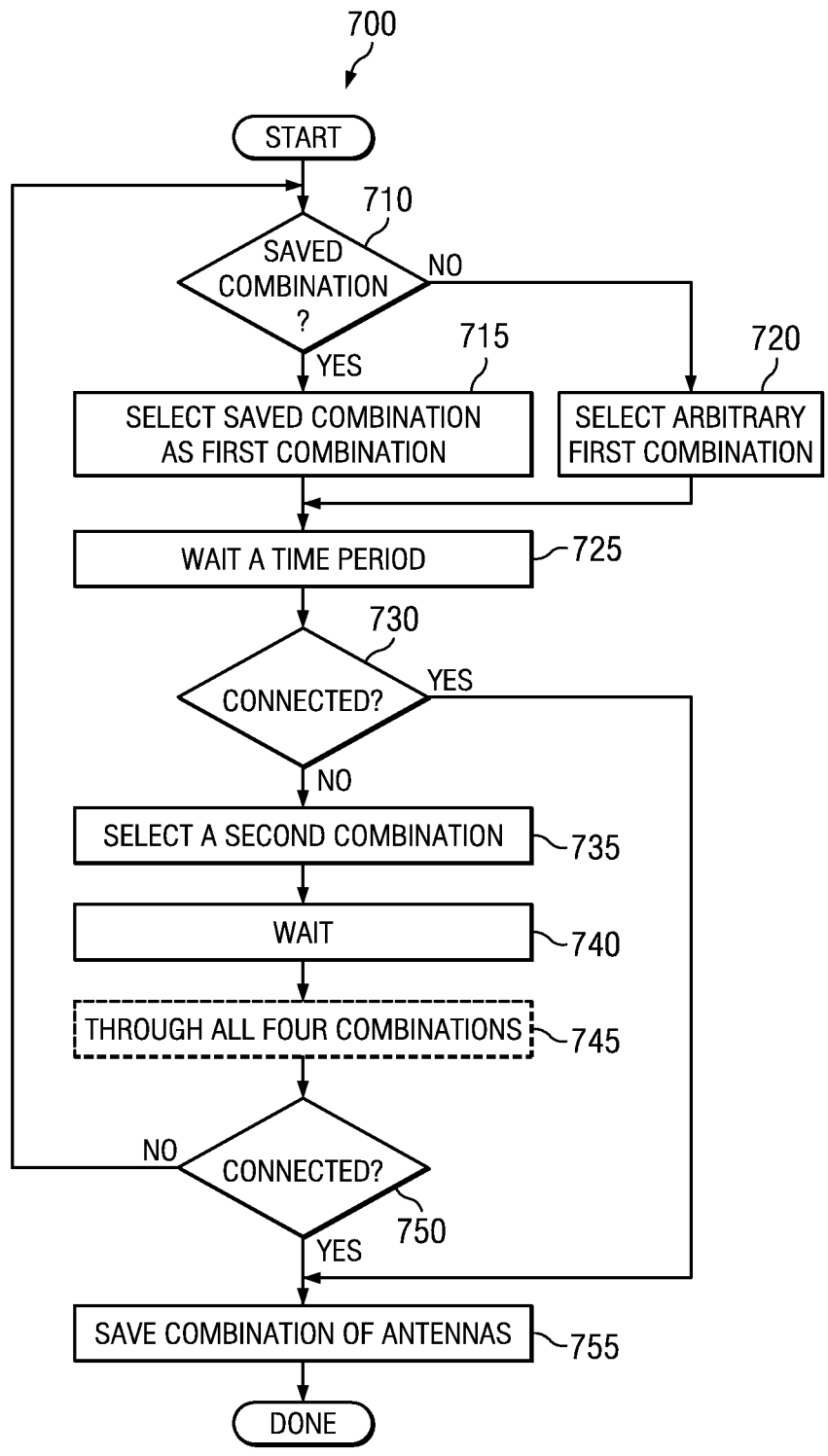
FIG. 9 is a method of operating the programmer of FIG. 3 according to some embodiments.

FIG. 9 is a flowchart depicting a method 700 for selecting antennas while establishing a connection. The method 700 is executed simultaneously with the wireless communication device's wakeup and connection-establishment procedure. The method 700 starts with step 710 by checking whether there is a saved combination of antennas from a previous communications session. If there is, the method 700 proceeds to step 715 and sets the antennas to this saved combination. If there is not, the method 700 proceeds to step 720 and sets the antennas to an arbitrary first combination.

The method 700 then proceeds to step 725 and waits a period of time and checks whether the wireless communication device has established a connection at step 730. If the wireless communication device has not established a connection, the method 700 proceeds to step 735 to select a second combination of antennas different from the first combination. The method 700 then proceeds to step 740 to wait a period of time, and checks to see if a connection has been established. The method 700 repeats steps 730, 735, and 740 for the remaining combinations such that all four combinations may be tried, at step 745, then loops back to the beginning of the method at step 710. However, once any of the checks for connection at step 730 or step 750 indicates a connection, the method 700 will save the combination of the antennas that was successful in establishing the connection at step 755 and then terminates. The saved combination of antennas becomes the first combination used the next time the method 700 is performed.

After connection establishment, the programmer needs to be able to change antennas during communications. People are not very good at holding still, and as a result, the programmer and the implanted medical device are both likely to move in their environment during communications. That movement can cause multipath fading. Furthermore, the person holding the programmer may shift her grip and obscure an antenna or reveal a previously-obscured antenna. To keep communications reliable despite this changing environment, the CPU in the programmer continuously monitors the communications link quality and switches main antennas if the link quality drops to an unacceptable level.

Figure 10:
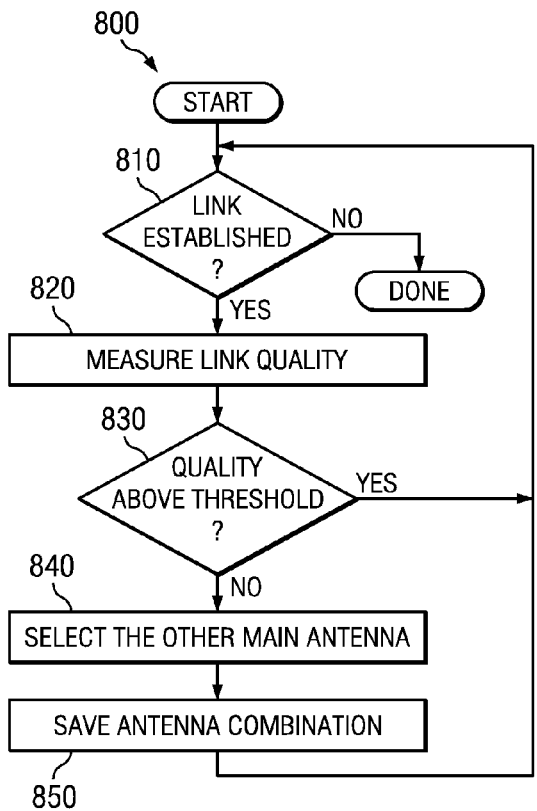
FIG. 10 is a method of operating the programmer of FIG. 3 according to some embodiments.

FIG. 10 is a flowchart of a method 800 used by the programmer to switch antennas during communications. The method 800 begins with step 810 to check whether the communications link is still established. If it is not, the method 800 terminates. If the communications link is established, the method 800 proceeds to step 820 to read values from the wireless communication device and determine a metric of link quality. This link quality is compared to a threshold value in step 830. If the quality is above the threshold, the method 800 returns to the beginning. If the quality metric is below the threshold, however, the programmer switches to the other main antenna in step 840. The new combination of antennas (with the wakeup antenna used during establishment and the new selection of main antenna) is saved in step 850 for use by the connection-establishment method 700 of FIG. 8. Thereafter, the method 800 restarts at the beginning. The method 800 keeps running as long as the connection is established.

The link quality metric can be obtained in several ways. First, the number of packet retransmissions may be used. Second, the number of bit errors corrected may be used. Third, whether any packet reached the retransmission limit and was dropped may be used. Finally, a combination of these values may be used. In particular, the number of packet retransmissions or the number of bit errors corrected can be given a link quality score that could be above or below the threshold, but the presence of any dropped packets from an exceeded retransmission limit may result in a link quality score that is always below the threshold. Other variations are also possible.

It is understood that the programmer discussed above applies to either a clinician programmer or a patient programmer, as well as to any other suitable device that is operable to control an implanted medical device in an uncontrolled or variable environment.

Figure 11:
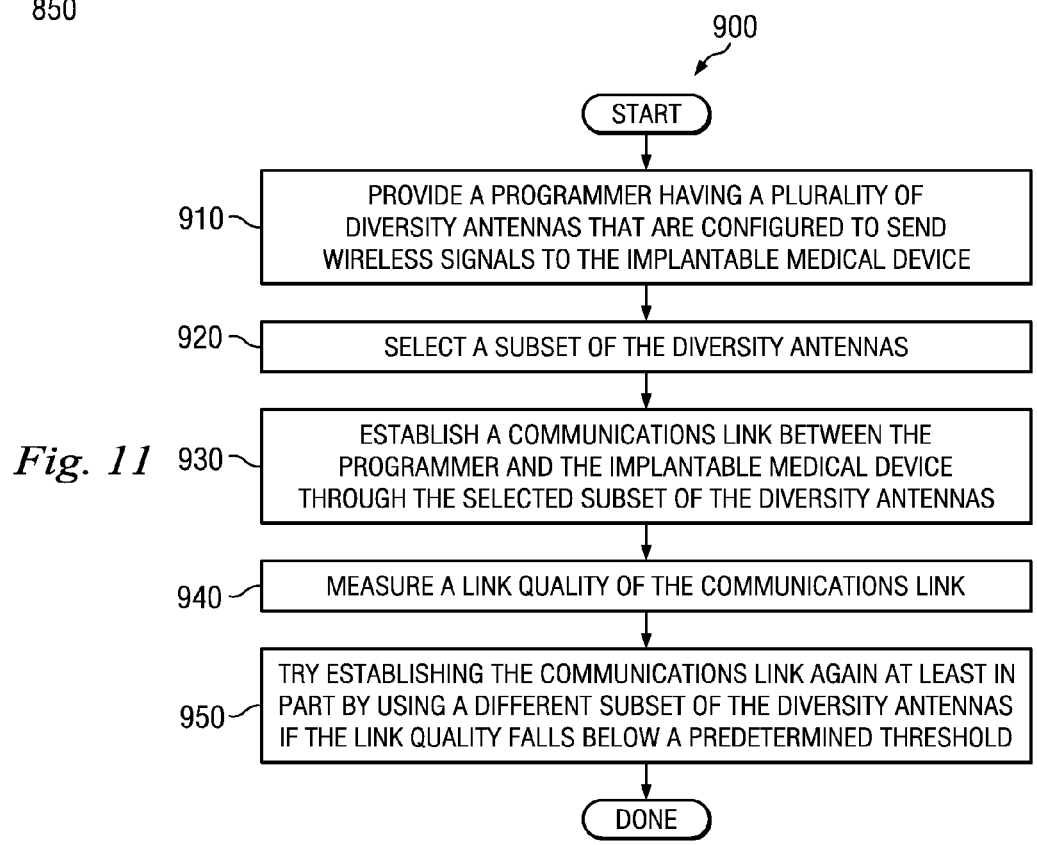
FIG. 11 is a method of operating the programmer of FIG. 3 according to some embodiments.

FIG. 11 is a flowchart of a method 900 of operating a programmer that communicates with an implanted medical device according to various aspects of the present disclosure. The method 900 includes a step 910 in which a programmer having a plurality of diversity antennas is provided. The diversity antennas are configured to send wireless signals to the implanted medical device. In some embodiments, the diversity antennas include a first group of antennas dedicated to a first frequency band and a second group of antennas dedicated to a second frequency band. In some embodiments, the programmer includes a first wireless communication device configured to communicate with the implantable medical device in the first frequency band through the first group of antennas, and the programmer includes a second wireless communication device configured to communicate with the implantable medical device in the second frequency band through the second group of antennas. In some embodiments, at least some of the diversity antennas have diverse locations on the programmer, at least some of the diversity antennas have diverse physical orientations, and at least some of the diversity antennas have diverse physical attributes with respect to size and geometry.

The method 900 includes a step 920 in which a subset of the diversity antennas is selected to perform communications with the implanted medical device. In some embodiments, the step 920 includes determining whether a saved subset of diversity antennas exists. If the saved subset exists, the saved subset is selected. If the saved subset does not exist, the step 920 includes trying different combinations of diversity antennas until a particular combination of antennas has been verified to be capable of maintaining a connection between the programmer and the medical device, and selecting the particular combination of antennas as the selected subset. In some embodiments, the step 920 is performed at least in part using one or more diversity switches on the programmer.

The method 900 includes a step 930 in which a communications link is established between the programmer and the implantable medical device through the selected subset of the diversity antennas. The method 900 includes a step 940 in which a link quality of the communications link is measured. In some embodiments, the step 940 is performed based one or more factors selected from the group consisting of: a number of packet retransmissions, a number of bit errors corrected, and whether any packet reached a retransmission limit and was dropped. The method 900 includes a step 950 in which a different subset of the diversity antennas is selected to communicate with the implantable medical device if the link quality falls below a predetermined threshold.

Figure 12A:
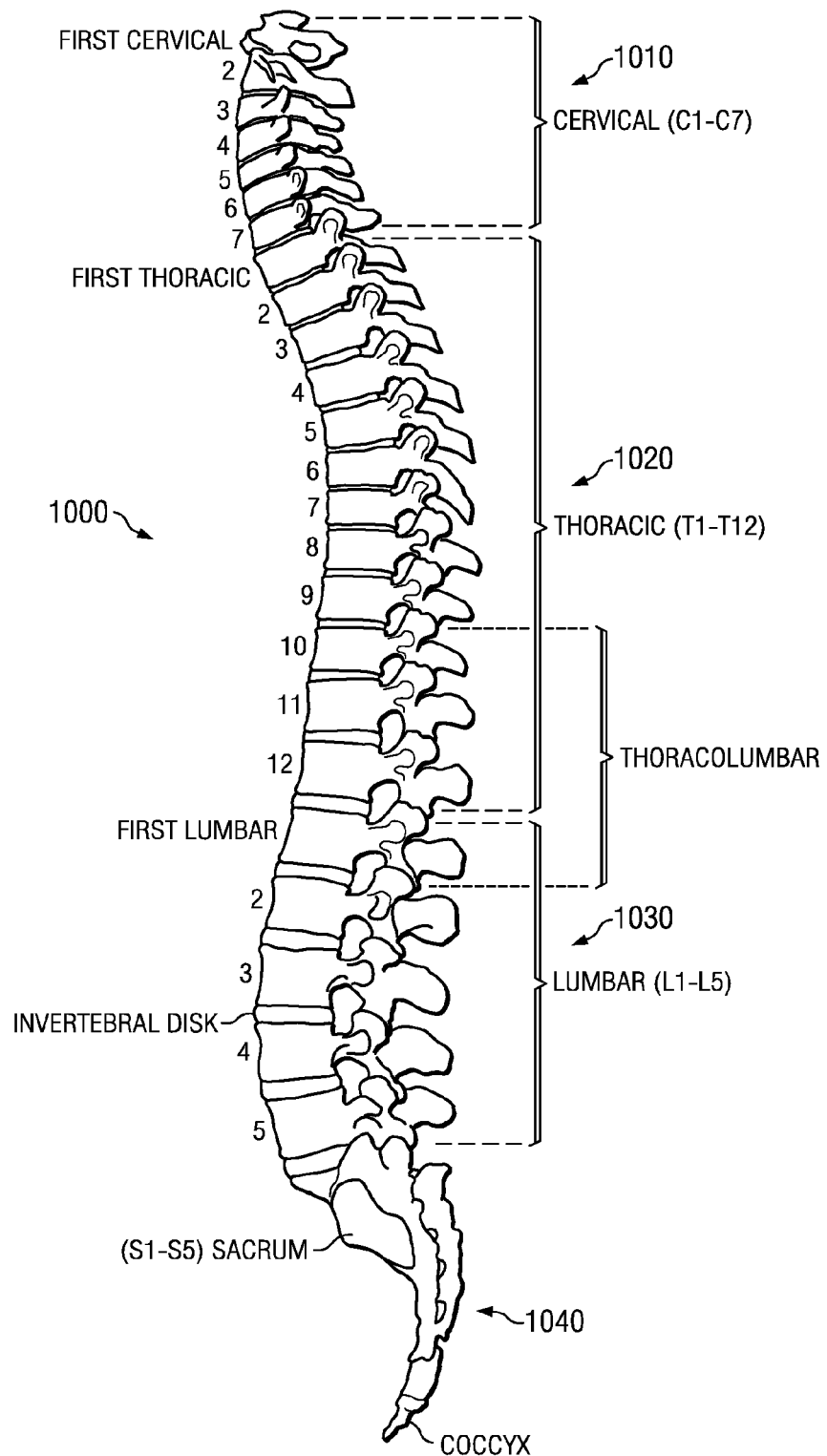
FIGS. 12A and 12B are side and posterior views of a human spine, respectively.
Figure 12B:
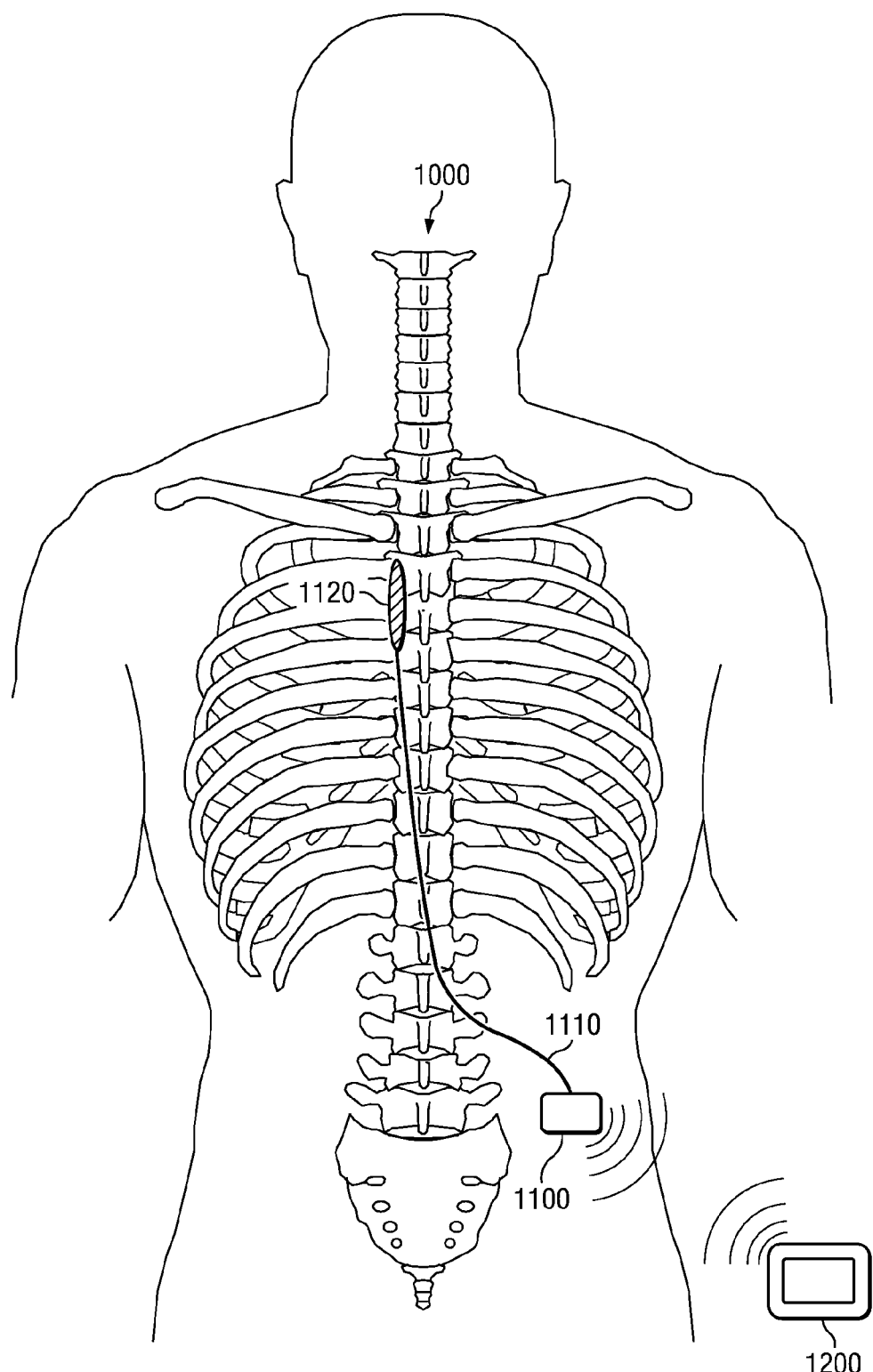

FIG. 12A is a side view of a spine 1000, and FIG. 12B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 12B, an IPG device 1100 is implanted inside the body. The IPG device 1100 may include various embodiments of the neurostimulator device 120 described above. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation: prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of communicating with an implantable medical device, comprising:
   providing a programmer having a plurality of diversity antennas, the diversity antennas being configured to send wireless signals to the implantable medical device;
   selecting a subset of the diversity antennas, wherein the selecting the subset of the diversity antennas comprises:
      determining whether a saved subset of diversity antennas exists;
      if the saved subset exists, selecting the saved subset as an initial subset;
      if the saved subset does not exist, selecting an arbitrary subset as the initial subset;
      trying different combinations of diversity antennas, starting with the initial subset, until a particular combination of antennas has been verified to be capable of maintaining a connection between the programmer and the medical device; and
      selecting the particular combination of antennas as the selected subset;
   establishing a communications link between the programmer and the implantable medical device through the selected subset of the diversity antennas;
   measuring a link quality of the communications link; and selecting a different subset of the diversity antennas to communicate with the implantable medical device if the link quality falls below a predetermined threshold.

2. The method of claim 1, wherein the diversity antennas include:
   a first group of antennas dedicated to a first frequency band; and
   a second group of antennas dedicated to a second frequency band.

3. The method of claim 2, wherein the programmer comprises:
   a first wireless communication device configured to communicate with the implantable medical device in the first frequency band through the first group of antennas; and
   a second wireless communication device configured to communicate with the implantable medical device in the second frequency band through the second group of antennas.

4. The method of claim 2, wherein the antennas in at least one of the first and second groups have different radiation patterns from the rest of the antennas in that group.

5. The method of claim 1, wherein at least some of the diversity antennas have diverse locations on the programmer.

6. The method of claim 1, wherein at least some of the diversity antennas have diverse physical orientations.

7. The method of claim 1, wherein at least some of the diversity antennas have diverse physical attributes with respect to size and geometry.

8. The method of claim 1, further comprising: repeating the establishing the communications link performed at least in part by using one or more diversity switches on the programmer.

9. The method of claim 1, wherein the measuring the link quality is performed based one or more factors selected from the group consisting of: a number of packet retransmissions, a number of bit errors corrected, and whether any packet reached a retransmission limit and was dropped.

10. The method of claim 1, wherein the antennas are implemented on a circuit board disposed within the electronic programmer.

11. A method of communicating with an implantable medical device, comprising:
   selecting a first subset of a plurality of antennas, wherein the plurality of antennas are located on a circuit board of an electronic programmer for an implantable medical device and are configured to conduct wireless communication with the implantable medical device, wherein the selecting the first subset of the antennas comprises:
      determining whether a saved subset of antennas exists;
      if the saved subset exists, selecting the saved subset as an initial subset;
      if the saved subset does not exist, selecting an arbitrary subset as the initial subset;
      trying different combinations of antennas, starting with the initial subset, until a particular combination of antennas has been verified to be capable of maintaining a connection between the electronic programmer and the medical device; and
      selecting the particular combination of antennas as the first subset;
   forming a communications link between the electronic programmer and the implantable medical device through the first subset of antennas;
   measuring a quality of the communications link; and
   selecting a second subset of the antennas to communicate with the implantable medical device if the measured quality of the communications link is less than a predetermined threshold, wherein the second subset is different from the first subset.

12. The method of claim 11, wherein the plurality of antennas include:
   a first group of antennas dedicated to a first frequency band; and
   a second group of antennas dedicated to a second frequency band.

13. The method of claim 12, wherein the antennas in at least one of the first and second groups have different radiation patterns from the rest of the antennas in that group.

14. The method of claim 11, wherein the electronic programmer comprises:
   a first radio configured to communicate with the implantable medical device in the first frequency band through the first group of antennas; and
   a second radio configured to communicate with the implantable medical device in the second frequency band through the second group of antennas.

15. The method of claim 11, wherein at least some of the plurality of antennas have different locations on the electronic programmer, or different physical orientations, or different physical attributes with respect to size and geometry.

16. The method of claim 11, wherein the measuring the quality of the communications link is performed based one or more factors selected from the group consisting of: a number of packet retransmissions, a number of bit errors corrected, and whether any packet reached a retransmission limit and was dropped.

17. A method of communicating with an implantable medical device, comprising:
   selecting a first subset of a plurality of antennas, wherein the plurality of antennas are located on an electronic programmer for an implantable pulse generator (IPG) and are configured to conduct wireless communication with the IPG, wherein at least some of the plurality of antennas have different locations on the electronic programmer, or different physical orientations, or different physical attributes with respect to size and geometry, wherein the selecting the first subset of the antennas comprises:
      determining whether a saved subset of antennas exists;
      if the saved subset exists, selecting the saved subset as an initial subset;
      if the saved subset does not exist, selecting an arbitrary subset as the initial subset;
      trying different combinations of antennas, starting with the initial subset, until a particular combination of antennas has been verified to be capable of maintaining a connection between the electronic programmer and the medical device; and
      selecting the particular combination of antennas as the first subset;
   establishing a communications link between the electronic programmer and the IPG through the first subset of antennas;
   evaluating a quality of the communications link, wherein the quality of the communications link is evaluated based one or more of the following factors: a number of packet retransmissions, a number of bit errors corrected, and whether any packet reached a retransmission limit and was dropped; and
   selecting a second subset of the antennas to support the communications link with the IPG in response to the quality of the communications link falling below a predetermined threshold, wherein the second subset is different from the first subset.

18. The method of claim 17, wherein:
the plurality of antennas include:
- a first group of antennas dedicated to a first frequency band; and
- a second group of antennas dedicated to a second frequency band; and the electronic programmer comprises:
- a first radio configured to communicate with the IPG in the first frequency band through the first group of antennas; and
- a second radio configured to communicate with the IPG in the second frequency band through the second group of antennas.

19. The method of claim 18, wherein the antennas in at least one of the first and second groups have different radiation patterns from the rest of the antennas in that group.

20. The method of claim 17, wherein the plurality of antennas are implemented on a printed circuit board (PCB) inside the electronic programmer.

* * * * *